United States Patent [19]

Gill

[11] Patent Number: 5,074,301
[45] Date of Patent: Dec. 24, 1991

[54] APPARATUS AND METHOD FOR ATRIAL PACE BEFORE VENTRICULAR SHOCK IN DUAL CHAMBER ARRHYTHMIA CONTROL SYSTEM

[75] Inventor: Norma L. Gill, Elanora Heights, Australia

[73] Assignee: Telectronics Pacing Systems, Inc., Tucson Way, Colo.

[21] Appl. No.: 552,827

[22] Filed: Jul. 16, 1990

[51] Int. Cl.$^5$ .............................................. A61N 1/39
[52] U.S. Cl. .......................... 128/419 D; 128/419 PG
[58] Field of Search ...................... 128/419 D, 419 PG

[56] References Cited

U.S. PATENT DOCUMENTS

| | | | |
|---|---|---|---|
| 3,566,876 | 3/1971 | Stoft et al. | 128/419 D |
| 3,857,398 | 12/1974 | Rubin | 128/419 D |
| 4,384,585 | 5/1983 | Zipes | 128/419 D |
| 4,850,357 | 7/1989 | Bach, Jr. | 128/419 D |
| 4,869,252 | 9/1989 | Gilli | 128/419 PG |
| 4,895,151 | 1/1990 | Grevis et al. | 128/419 PG |
| 5,007,422 | 4/1991 | Pless et al. | 128/419 D |

OTHER PUBLICATIONS

Saksena et al., "Comparative Efficacy of Transvenous Cardioversion and Pacing in Patients With Sustained Ventricular Tachycardia: A Prospective Randomized Crossover Study", *Circulations*, vol. 72, No. 1, pp. 153-160 (1985).

Saksena and Calvo, "Transvenous Cardioversion and Defibrillation of Ventricular Tachyarrhythmias: Current Status and Future Directions", *PACE*, vol. 8, pp. 715-731 (1985).

Primary Examiner—Kyle L. Howell
Assistant Examiner—Kennedy J. Schoetzle
Attorney, Agent, or Firm—Gottlieb, Rackman & Reisman

[57] ABSTRACT

An apparatus and method for tachyarrhythmia reversion provides a pacing pulse to the atrium at a predetermined time prior to the delivery of a cardioversion shock to the ventricle. The pacing pulse depolarizes the atrium producing an atrial refractory period. The cardioversion shock therapy is delivered during this refractory period in order to avoid the vulnerable zone of the atrium. This minimizes post-shock arrhythmias attributable to shock delivery during the atrial vulnerable zone. When used with bradycardia support pacing, a post-shock therapy pacing delay or pause is introduced, following reversion of the tachyarrhythmia, before delivering the bradycardia support pacing. The magnitude of the delay period is substantially greater than the normal bradycardia support pacing standby interval.

27 Claims, 5 Drawing Sheets

APPARATUS AND METHOD FOR ATRIAL PACE BEFORE VENTRICULAR SHOCK IN DUAL CHAMBER ARRHYTHMIA CONTROL SYSTEM

TECHNICAL FIELD

This invention relates to implantable medical devices which monitor the cardiac state of a patient by sensing sinus rhythm, ventricular tachycardia and ventricular fibrillation and which deliver therapy in the form of electrical energy to cardiac tissue to revert tachycardia and restore sinus rhythm.

As used herein antitachycardia pacing refers to any pacing for the reversion of tachycardia. The term tachyarrhythmia refers to any fast abnormal rhythm of the heart which may be amenable to treatment by electrical discharges. This specifically includes ventricular tachycardia (VT), supraventricular tachycardia (SVT), ventricular flutter and ventricular fibrillation (VF), atrial tachycardia (AT), and atrial flutter and atrial fibrillation (AF).

The term therapy as used herein includes the processes used between the detection and the reversion of a tachyarrhythmia and includes the actions of antitachycardia pacing, cardioversion and/or defibrillation shocks. The term cardioversion refers to the discharge of electrical energy into the cardiac tissue in an attempt to terminate or revert a tachyarrhythmia. This may take the form of a high energy discharge (up to 40 Joules or more) or a low energy discharge (less than 1 Joule). The discharge may be monophasic or biphasic but is not restricted to these waveforms. Cardioversion shocks may or may not be synchronized to the rhythm of the heart. Defibrillation is a particular example of cardioversion.

This invention applies equally to devices which deliver energy synchronized to an R-wave and to those that do not, and it applies to devices which use lower energy pulses as well as to devices which use higher energy pulses. The invention applies to devices which deliver cardioverting shocks alone as well as to devices which deliver cardioverting shocks in combination with antitachycardia pacing pulses. The invention will usually apply to implantable multiple chamber cardioverters or defibrillators, but is equally applicable to ventricular cardioverters or atrial cardioverters. The invention applies also to the delivery of any antitachycardia pacing pulses and post reversion pacing therapy.

BACKGROUND ART

U.S. Pat. No. 3,857,398 to Rubin, entitled "Electrical Cardiac Defibrillator", describes a combined cardiac pacer and defibrillator device which performs a pacing or a defibrillating function depending on the condition detected. When the device detects tachycardia, it switches to a defibrillating mode and, after a period of time during which a charge is accumulated, delivers a defibrillation shock to the patient. When the device detects that the heart rate has fallen below a predetermined value, the pacer switches to a demand pacing mode and delivers pacing pulses to the heart.

A multiprogrammable, telemetric, implantable defibrillator is disclosed in the copending U.S. patent application Ser. No. 239,624 of Norma Louise Gilli et al., filed Sept. 1, 1988, entitled "Reconfirmation Prior To Shock In Implantable Defibrillator," which is assigned to the assignee of the present invention. This device contains a bradycardia support system as well as a high energy shock system to revert ventricular tachycardia to normal sinus rhythm. After reconfirmation of the presence of a tachycardia, high energy shock is delivered to the patient either at a predetermined time or when the desired energy level is reached.

Supraventricular tachycardias have been observed following termination of ventricular tachycardia by either cardioversion or antitachycardia pacing, as described in the article "Comparative Efficacy of Transvenous Cardioversion and Pacing in Patients With Sustained Ventricular Tachycardia: A Prospective, Randomized, Crossover Study" by Saksena et al. in *Circulation*, Vol. 72, No. 1, pp. 153-160 (1985). Termination with transvenous cardioversion was followed by occurrences of atrial fibrillation, atrial flutter, and sinus tachycardia.

Post cardioversion arrhythmias have also been observed by Saksena and Calvo, as referred to in the article "Transvenous Cardioversion and Defibrillation of Ventricular Tachyarrhythmias: Current Status and Future Directions" in *PACE*, Vol. 8, pp. 715-731 (1985). In this study, the incidence of supraventricular tachyarrhythmias after transvenous cardioversion was substantial.

DISCLOSURE OF THE INVENTION

It is therefore apparent that the heart is susceptible to arrhythmias after cardioversion antitachyarrhythmia therapy. In patients receiving cardioversion shocks using prior art devices, it has been observed in some cases that such post therapy arrhythmias have been attributable to the shock being delivered during the vulnerable zone of the atrium. In those cases where post therapy atrial arrhythmias occur there is the likelihood of this arrhythmia being detected as ventricular tachycardia or ventricular fibrillation, resulting in the patient receiving an unnecessary shock.

It is an object of the invention to reduce the likelihood of reinducing or inducing an arrhythmia by pacing the atrium immediately prior to delivering a ventricular shock. The pacing pulse depolarizes the atrium, producing an atrial refractory period. The delivery of cardioversion shock therapy during this refractory period assures that the vulnerable zone of the atrium is avoided, thereby minimizing post-shock arrhythmias attributable to shock delivery during the atrial vulnerable zone.

According to another feature of the invention, there is provided an implantable combined dual chamber pacing and cardioverting device for the reversion of tachyarrhythmia, including bradycardia support pacing means for both the atrium and the ventricle. The device includes means for detecting the presence of a tachyarrhythmia and means responsive to such detection for delivering a pacing pulse to the atrium to depolarize the atrium, thereby producing for a period of time an atrial refractory condition. The device also includes means responsive to such detection for delivering cardioversion shock therapy during such atrial refractory period, whereby both the atrium and the ventricle are simultaneously in a refractory condition immediately following the discharge of the cardioversion shock. In a preferred embodiment of the invention the device also includes means for switching to bradycardia support pacing after a post therapy delay period of time that is substantially longer than the normal bradycardia support pacing standby interval.

The invention also provides a method of reverting tachyarrhythmia. The method includes detecting the presence of tachyarrhythmia and, upon such detection, delivering a pacing pulse to the atrium to depolarize the atrium and produce for a limited period of time an atrial refractory condition. The method further includes delivering cardioversion shock therapy during the atrial refractory period which follows delivery of the pacing pulse. In a preferred version of the method bradycardia support pacing is instituted after a post therapy delay period of time that is substantially longer than the normal bradycardia support pacing standby interval. This delay period is usually between substantially two and substantially five seconds, and is preferably between three and four seconds.

BRIEF DESCRIPTION OF THE DRAWINGS

Further objects, features and advantages of the invention will become apparent upon consideration of the following detailed description in conjunction with the drawings, in which.

BEST MODE FOR CARRYING OUT THE INVENTION

Figure 1:
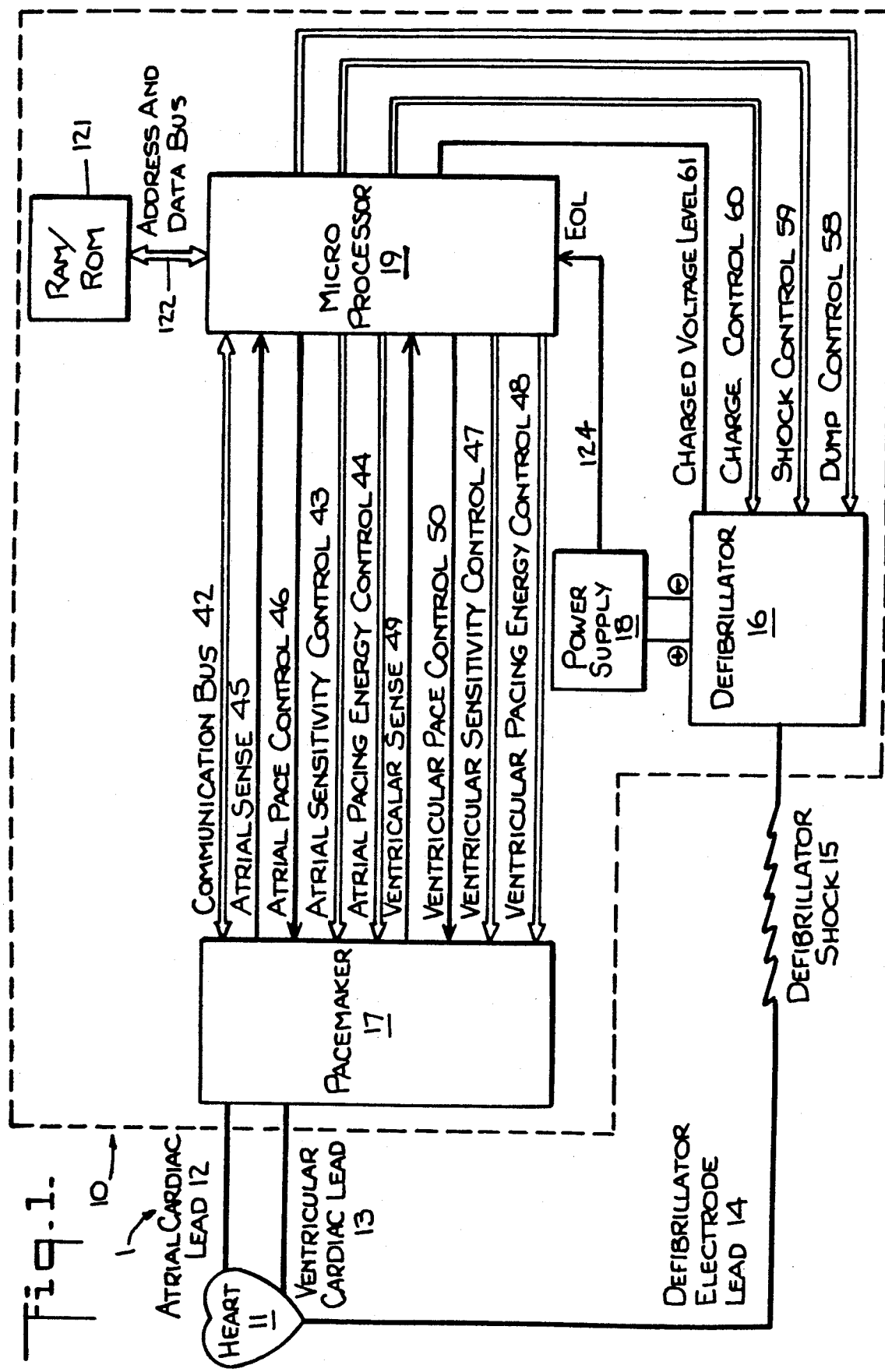
FIG. 1 is a block diagram of a dual chamber arrhythmia control system in which the present invention may be used.

Referring to FIG. 1, there is depicted a block diagram of an arrhythmia control system 1. System 1 is designed to be implantable in a patient and includes a pulse module 10 and appropriate leads for connecting module 10 to a patient's heart 11. More particularly, system 1 will generally include an atrial cardiac lead 12 extending to the atrium of the patient's heart for the administration of therapy to the atrium and a ventricular cardiac lead 13 extending to the ventricle of the patient's heart for the administration of therapy to the ventricle. System 1 generally also includes a pacemaker 17 for the detection of analog signals representing cardiac electrical activity and for the delivery of pacing pulses to the heart; a microprocessor 19 which, in response to various inputs received from the pacemaker 17 as well as from a defibrillator 16, performs various operations so as to generate different control and data outputs to both pacemaker 17 and defibrillator 16; and a power supply 18 for the provision of a reliable voltage level to pacemaker 17, microprocessor 19 and defibrillator 16 by suitable electrical conductors (not shown). Defibrillator 16 produces a high voltage to charge its capacitors and then discharges them in response to control signals from microprocessor 19. A defibrillator electrode lead 14 transfers the energy of a defibrillator shock 15 from the implanted pulse module 10 to the surface of the heart 11.

Microprocessor 19 is connected to a RAM/ROM unit 121 by an address and data bus 122. An end-of-life (EOL) signal line 124 is used to provide, to microprocessor 19, a logic signal indicative of the approach of battery failure in power supply 18.

As more fully described below, microprocessor 19 and pacemaker 17 are connected by a communication bus 42, an atrial sense line 45, an atrial pace control line 46, an atrial sensitivity control bus 43, an atrial pace energy control bus 44, a ventricular sense line 49, a ventricular pace control line 50, a ventricular sensitivity control bus 47, and a ventricular pace energy control bus 48. As also more fully described below, microprocessor 19 is connected to defibrillator 16 by a charged voltage level line 61, a charge control bus 60, a shock control bus 59, and a dump control bus 58.

Figure 2:
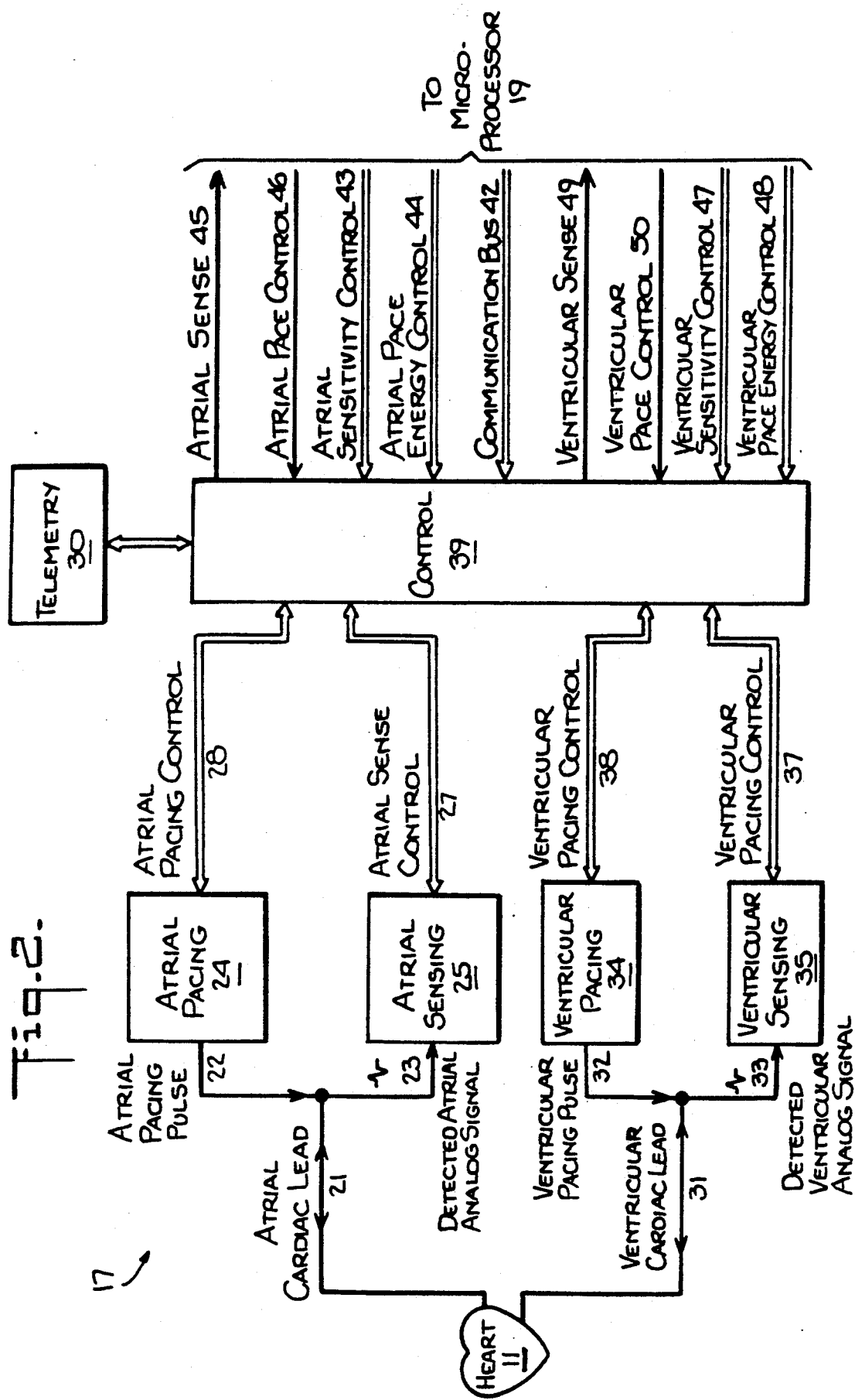
FIG. 2 is a block diagram of the pacemaker employed in FIG. 1.

Referring to FIG. 2, pacemaker 17 comprises circuitry for atrial pacing 24, ventricular pacing 34, atrial sensing 25, ventricular sensing 35, and telemetry 30. In addition, pacemaker 17 includes a control block 39 which includes an interface to microprocessor 19.

In operation, sensing circuits 25 and 35 detect respective atrial and ventricular analog signals 23 and 33 from the heart 11 and convert the detected signals to digital signals. In addition, the sensing circuits 25 and 35 receive an input atrial sense control 27 and an input ventricular sense control 37, respectively, from the control block 39 which determines the sensitivity applied to the detection circuit. As more fully described below, a change in this sensitivity will affect the voltage deviation required at the sensing electrode for a sense to be registered. The operation of the logic which changes the sensitivity is described in greater detail in the co-pending U.S. patent application Ser. No. 187,797 of Richard Grevis and Norma Louise Gilli, filed Apr. 29, 1988, entitled "Apparatus And Method For Controlling Multiple Sensitivities In Arrhythmia Control System Including Post Therapy Pacing Delay," which is assigned to the assignee of the present invention and is incorporated herein by reference.

Atrial pacing circuit 24 receives from control block 39 via an atrial pacing control bus 28 an atrial pace control input and an atrial pacing energy control input. Similarly, ventricular pacing circuit 34 receives from control block 39 via a ventricular pacing control bus 38 a ventricular pace control input and a ventricular pacing energy control input. The atrial and ventricular pace control inputs determine the respective types of atrial and ventricular pacing to occur, while the atrial and ventricular pacing energy control inputs determine the respective magnitudes of the pulse energy. The operation of the logic which changes the pulse energy is described in greater detail in U.S. Pat. No. 4,869,252 of Norma Louise Gilli, issued Sept. 26, 1989, entitled "Apparatus And Method For Controlling Pulse Energy In Antitachyarrhythmia And Bradycardia Pacing Devices," which is assigned to the assignee of the present invention and is incorporated herein by reference.

Telemetry circuit 30 provides a bidirectional link between control block 39 of pacemaker 17 and an external device such as a programmer. It allows data such as the operating parameters to be read from or altered in the implanted pulse module 10.

Figure 3:
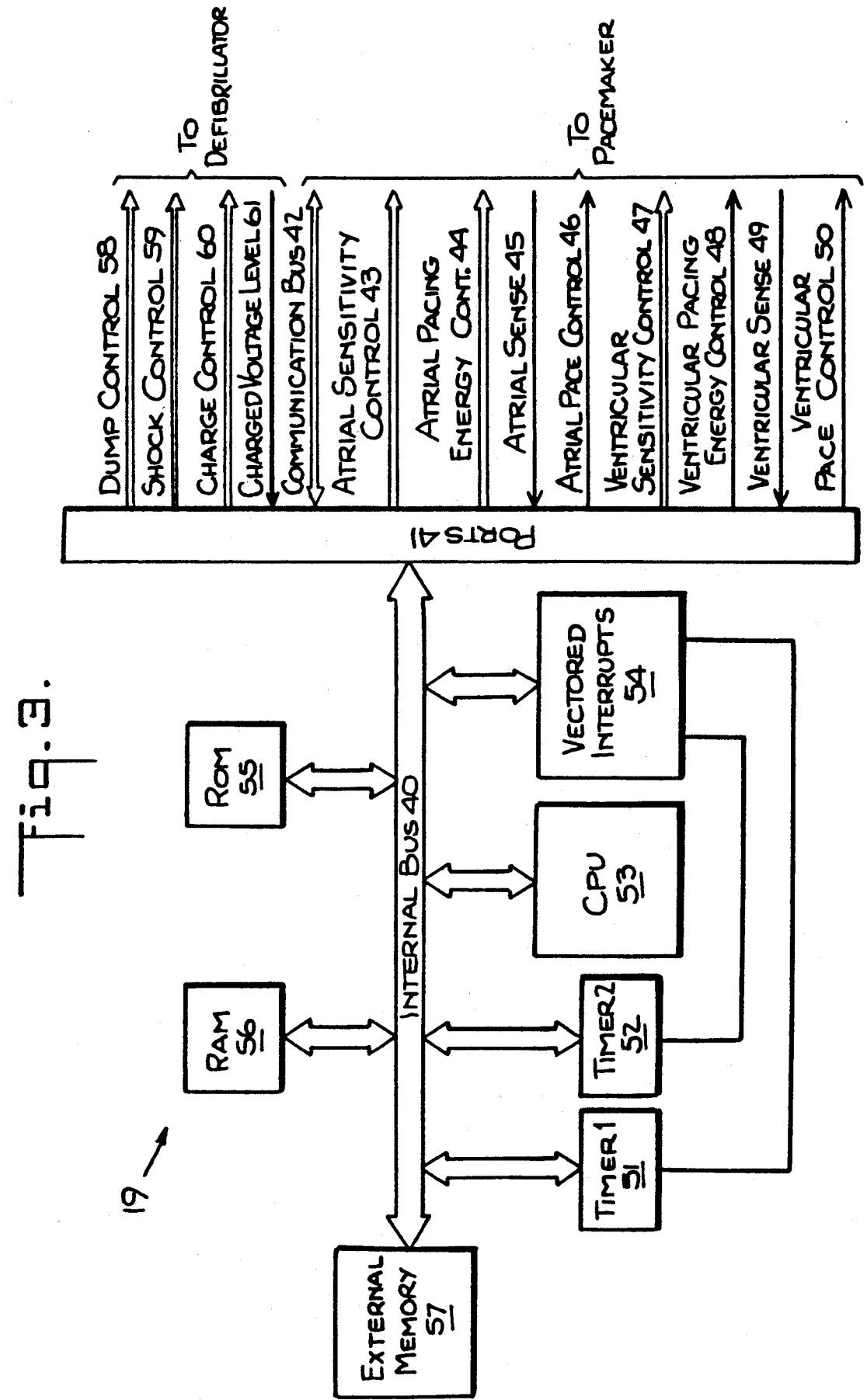
FIG. 3 is a block diagram of the microprocessor employed in FIG. 1.

Referring to FIG. 3, microprocessor 19 comprises two 16-bit timers 51 and 52, CPU 53, vectored interrupts block 54, ROM 55, RAM 56, external memory 57, ports 41 and an internal communications bus 40. RAM 56 acts as a scratch pad and active memory during execution of the various programs stored in ROM 55 and used by microprocessor 19. These programs include system supervisory programs, detection algorithms for detecting various arrhythmias, and programming implementing the logic flow diagram of FIG. 5, as well as storage programs for storing, in external memory 57, data concerning the functioning of module 10 and the electrogram provided by ventricular cardiac lead 13 (FIG. 1). Timers 51 and 52 and associated control software implement some timing functions required by microprocessor 19 without resort entirely to software, thus reducing computational loads on and power dissipation by CPU 53.

Signals received from telemetry circuit 30 permit an external programmer (not shown) to change the operating parameters of pacemaker 17 by supplying appropriate signals to control block 39. Communications bus 42 serves to provide signals indicative of such control to microprocessor 19. Thus, it is also possible for an external programmer to control operation of defibrillator 16 by means of signals provided to microprocessor 19.

Appropriate telemetry commands may cause telemetry circuit 30 to transmit data to the external programmer. Data stored is read out, by microprocessor 19, on to communications bus 42, through control block 39 in pacemaker 17, and into telemetry circuit 30 for transmission to the external programmer by a transmitter in telemetry circuit 30.

Microprocessor 19 receives various status and/or control inputs from pacemaker 17 and defibrillator 16, such as the sense signals on sense lines 45 and 49. It performs operations, such as arrhythmia detection, and produces outputs, such as the atrial pace control on line 46 and the ventricular pace control on line 50, which determine the type of pacing that is to take place. Other control outputs generated by microprocessor 19 include the atrial and ventricular pacing energy controls on lines 44 and 48, respectively, which determine the magnitude of the pulse energy, the shock control on line 59 which signals that a shock is to be delivered to the patient, the dump control on bus 58 which indicates that a shock is to be dumped at an internal load within the defibrillator, the charge control on bus 60 which determines the voltage level of the shock to be delivered, and the atrial and ventricular sensitivity controls on buses 43 and 47, respectively, which determine the sensitivity settings of the sensing circuits. Charged voltage level line 61 provides a digital signal representative of charge voltage from an analog to digital converter within defibrillator 16, thus providing a feedback loop which assures that a shock of proper energy level is delivered by defibrillator 16.

Figure 4:
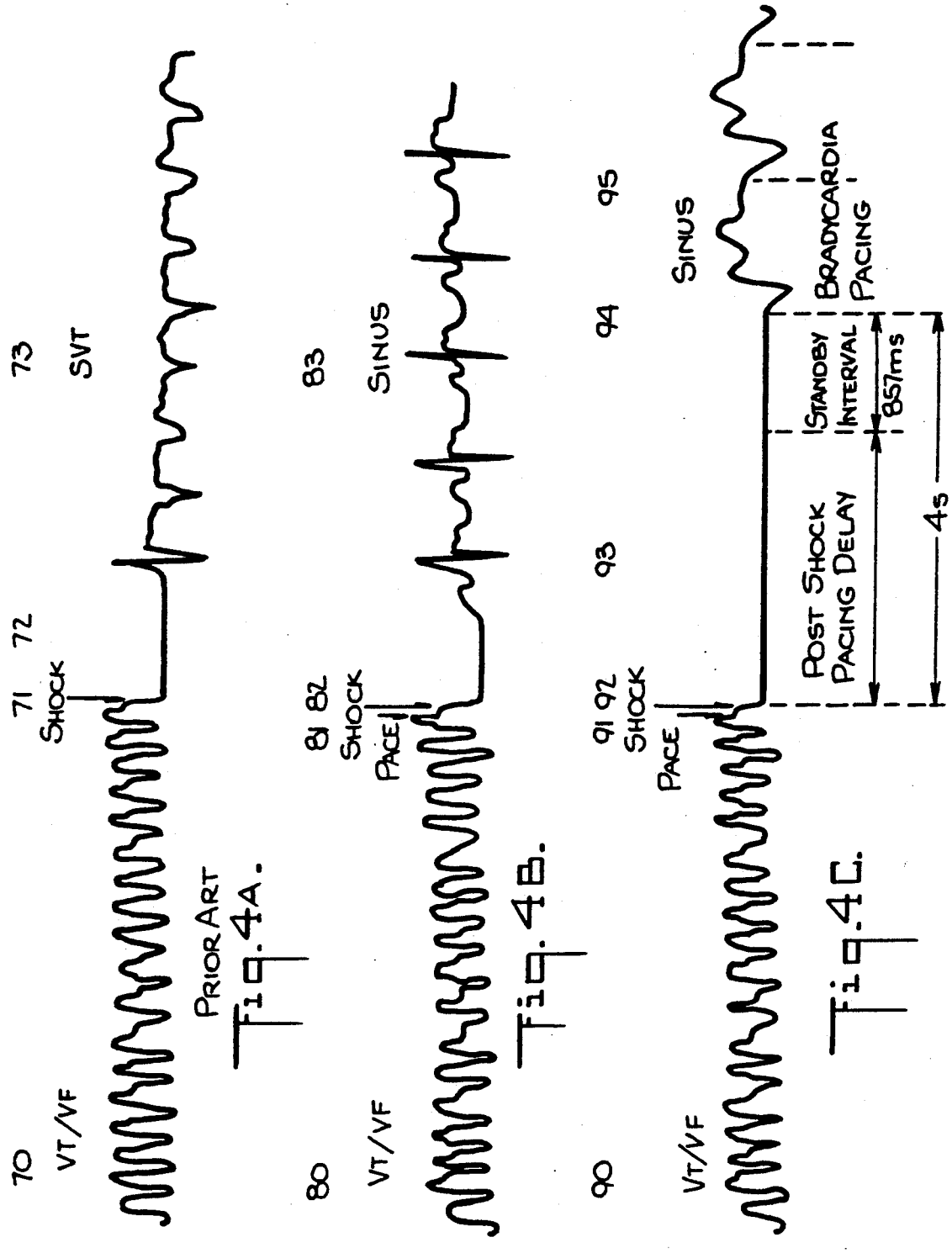
FIG. 4A depicts an ECG trace outlining a prior art defibrillation shock sequence wherein the defibrillation shock therapy is applied during the vulnerable zone of the atrium, without benefit of a pre-shock atrial pace.
FIG. 4B depicts another ECG trace outlining a defibrillation shock sequence in which the defibrillation shock therapy is preceded by a pre-shock atrial pace.
FIG. 4C depicts yet another ECG trace outlining a defibrillation shock sequence in which the defibrillation shock therapy is preceded by a pre-shock atrial pace and is followed by a post-shock delay and then by bradycardia support pacing following the post-shock delay; and, FIG. 5 is a logic flow diagram of the software executed by the microprocessor of FIG. 3 in accordance with the invention.

Referring to FIG. 4A, there is depicted an ECG trace outlining a prior art defibrillation shock sequence wherein the defibrillation shock therapy is applied during the vulnerable zone of the atrium, without the benefit of a pre-shock atrial pace. At 70, a VT/VF arrhythmia has developed. Defibrillation shock therapy is applied at 71. As shown at 72, the defibrillation shock has succeeded in reverting the VT/VF arrhythmia. However, by 73 a SVT arrhythmia has occurred due to the fact that the shock was delivered during the vulnerable zone of the atrium.

Referring to FIG. 4B, there is depicted an ECG trace outlining a defibrillation shock sequence in which the defibrillation shock therapy is preceded by a pre-shock atrial pace. At 80, a VT/VF arrhythmia has developed. Prior to the delivery of defibrillation shock therapy at 82, a pacing pulse is delivered to the atrium at 81. The timing of the pacing pulse is such that it renders the atrium depolarized during the subsequent delivery of the shock. The interval between the delivery of the pacing pulse and the delivery of the shock is usually short. In this embodiment, the interval is 100 ms but it may be longer or shorter than this value provided that the atrium is depolarized at the time of delivery of the ventricular shock. As shown at 83, the defibrillation shock has succeeded in reverting the VT/VF arrhythmia and normal sinus rhythm is present.

Referring to FIG. 4C, an ECG trace for a combined cardioverting and bradycardia support pacing device has been illustrated. The bradycardia support pacing portion of this device is preferably of the type described in the aforesaid copending U.S. patent application Ser. No. 187,797 of Richard Grevis and Norma Louise Gilli, filed Apr. 29, 1988. As seen in FIG. 4C, the ECG trace outlines a defibrillation shock sequence in which the defibrillation shock therapy is preceded by a pre-shock atrial pace and is followed by a post-shock delay prior to the initiation of bradycardia support pacing. At 90, a VT/VF arrhythmia has developed. A pacing pulse is delivered to the atrium at 91, which occurs about 100 ms prior to the delivery of defibrillation shock therapy at 92. This pacing pulse renders the atrium depolarized during the subsequent delivery of the shock.

As further shown in FIG. 4C, the defibrillation shock, which has succeeded in reverting the VT/VF arrhythmia, is followed by a post-shock delay, as shown at 93. At 94, asystole is detected and thus bradycardia pacing is commenced, about 4 seconds after the delivery of the defibrillation shock. By this time, the proarrhythmic effect of a premature recommencement of bradycardia support pacing immediately post reversion has been avoided, as there has been sufficient time for the patient's heart's conduction system to become reorganized and susceptible to bradycardia support pacing. The inhibiting of bradycardia support pacing for programmable or fixed periods of time (usually between substantially two and substantially five seconds, and preferably between three and four seconds) after antitachyarrhythmia defibrillation so as to avoid any proarrhythmic effect is described in greater detail in the aforesaid copending U.S. patent application Ser. No. 187,797 of Richard Grevis and Norma Louise Gilli, filed Apr. 29, 1988.

Figure 5:
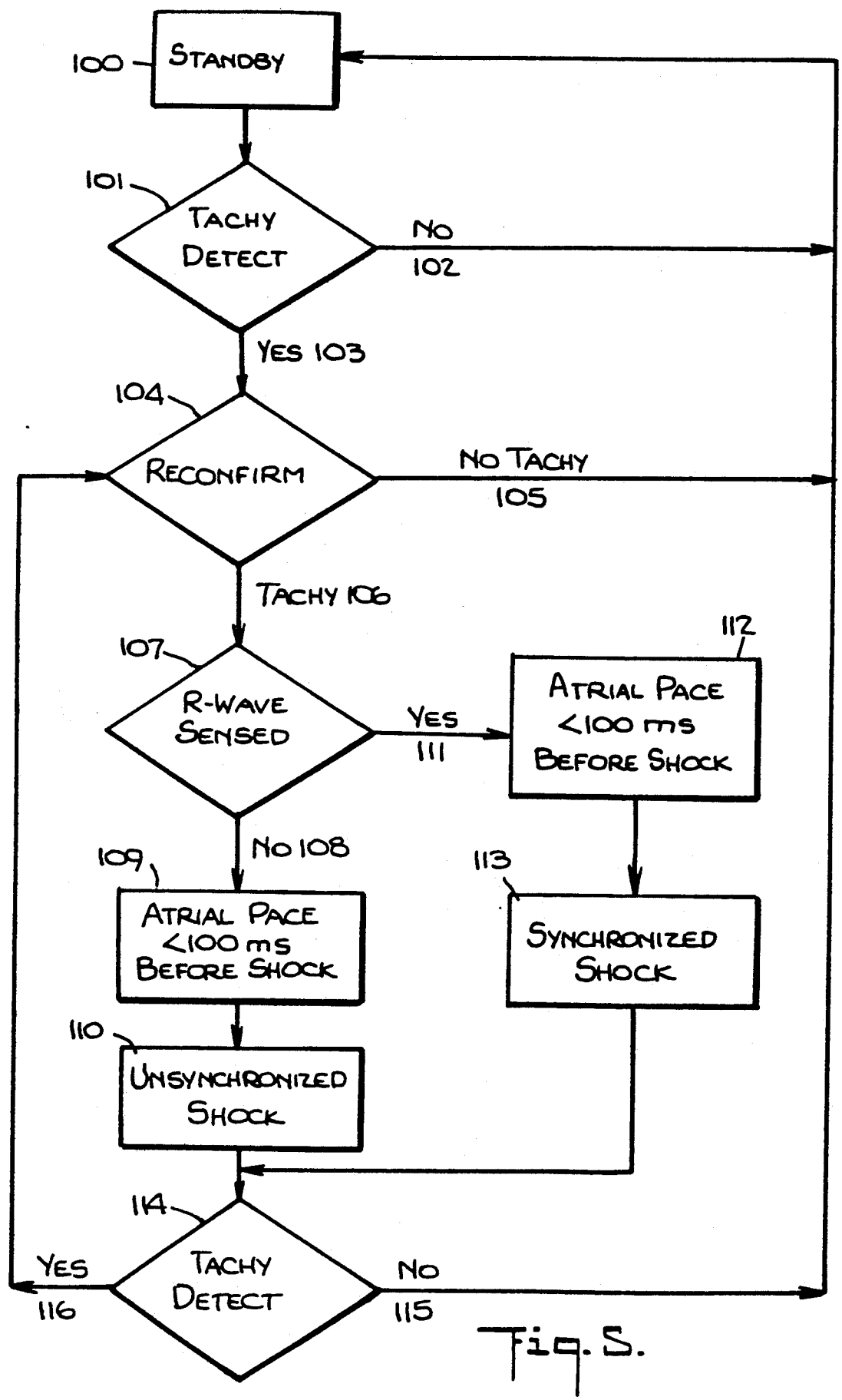

FIG. 5 is a logic diagram of the microprocessor flow control for controlling the operation of the arrhythmia control system 1, with the standby or start position being shown at 100. At 101, a determination is made as to whether tachyarrhythmia is detected or not. If tachyarrhythmia is not detected, as shown at 102, the program will loop back to the standby position 100, and there will be no change or delivering of therapy until the detection of tachyarrhythmia. If tachyarrhythmia is detected, as shown at 103, a decision with respect to tachyarrhythmia confirmation then takes place at 104. If tachyarrhythmia is not detected, as shown at 105, the program will loop back to 100, and there will be no change or delivering of therapy until the detection of tachyarrhythmia. If tachyarrhythmia has been confirmed, as shown at 106, then an attempt is made to sense the R-wave, as shown at 107.

If the R-wave is not sensed, as shown at 108, the program calls for an atrial pacing pulse, as shown at 109, and for an unsynchronized defibrillation shock, as shown at 110, to be delivered to the patient. The atrial pacing pulse delivered at 109 is timed to occur about 100 ms prior to the delivery of the defibrillation shock at 110.

If the R-wave is sensed, as shown at 111, the program calls for an atrial pacing pulse, as shown at 112, and for, in this case, a synchronized defibrillation shock, as shown at 113, to be delivered to the patient. The atrial pacing pulse delivered at 112 is delivered in synchronism with the R-wave. In addition, the timing of the atrial pacing pulse, relative to the defibrillation shock, is such that the defibrillation shock occurs about 100 ms after the atrial pacing pulse, during the atrial refractory period.

In either case, whether an unsynchronized shock, as at 110, or a synchronized shock, as at 113, is delivered to the patient, the program next calls for a determination to be made as to whether tachyarrhythmia is now present or not, as shown at 114. If tachyarrhythmia is not detected, as shown at 115, the program will loop back to the standby position 100, and there will be no further delivery of therapy until a subsequent detection of tachyarrhythmia occurs. If tachyarrhythmia is detected, as shown at 116, the program loops back to 104 for reconfirmation, and proceeds from that point in the manner described above in connection with point 104.

Although the invention has been described with reference to a particular embodiment, it is to be understood that this embodiment is merely illustrative of the application of the principles of the invention. For example, the delivery of a defibrillation shock following the detection of a tachyarrhythmia may be immediate or it may be dependent on the charge time of a capacitor. Alternatively, the time to the delivery of the shock may depend on the haemodynamic condition of the patient. In this regard, reference is made to the U.S. Pat. No. 4,895,151 of Lorraine Holley and Richard Grevis, issued Jan. 23, 1990, entitled "Apparatus And Method For Therapy Adjustment In Implantable Cardioverter", which is assigned to the assignee of the present invention and is incorporated herein by reference. Numerous other modifications may be made and other arrangements may be devised without departing from the spirit and scope of the present invention.

I claim:

1. An implantable cardioverting device adapted to be electrically connected to a patient's heart for the reversion of tachyarrhythmias, comprising:
   means for detecting the presence of a tachyarrhythmia;
   means responsive to the detection of a tachyarrhythmia by said detection means for delivering an atrial pacing pulse to the heart to depolarize the atrium and produce for a limited period of time an atrial refractory condition therein; and
   means responsive to the detection of said tachyarrhythmia by said detection means for delivering cardioversion shock therapy to the heart during the period of said atrial refractory condition, whereby both the atrium and the ventricle of the heart will be simultaneously in a refractory condition immediately following the delivery of the cardioversion shock therapy.

2. An implantable combined dual chamber pacing and cardioverting device adapted to be electrically connected to the atrium and the ventricle of a patient's heart for the reversion of tachyarrhythmias, comprising:
   means for providing bradycardia support pacing for both the atrium and the ventricle;
   means for detecting the presence of a tachyarrhythmia;
   means responsive to the detection of a tachyarrhythmia by said detection means for delivering a pacing pulse to the atrium to depolarize the atrium and produce for a limited period of time an atrial refractory condition therein; and
   means responsive to the detection of said tachyarrhythmia by said detection means for delivering cardioversion shock therapy to the heart during the period of said atrial refractory condition, whereby both the atrium and the ventricle will be simultaneously in a refractory condition immediately following the delivery of the cardioversion shock therapy.

3. A device according to claim 2, including means for delaying, for a post therapy delay period, the providing of bradycardia support pacing after said therapy means delivers said cardioversion shock therapy, said post therapy delay period being a period of time substantially longer than a normal bradycardia support pacing standby interval.

4. A device according to claim 3, wherein said post therapy delay period is between substantially two and substantially five seconds.

5. A device according to any one of claims 1-4, including means for synchronizing the delivery of said atrial pacing pulse with the R-wave of the heart.

6. A device according to any one of claims 1-4, including means for delivering antitachycardia pacing therapy to the atrium.

7. A device according to any one of claims 1-4, including means for delivering antitachycardia pacing therapy to the ventricle.

8. A device according to any one of claims 1-4, including means for delivering antitachycardia pacing therapy to both the atrium and the ventricle.

9. A device according to any one of claims 1-4, wherein said cardioversion shock therapy includes a monophasic waveform.

10. A device according to any one of claims 1-4, wherein said cardioversion shock therapy includes a biphasic waveform.

11. A device according to any one of claims 3 and 4, wherein said post therapy delay period is a fixed period of time.

12. A device according to any one of claims 3 and 4, wherein said post therapy delay period is a programmable parameter.

13. A device according to any one of claims 3 and 4, wherein said post therapy delay period is between substantially three and substantially four seconds.

14. A device according to any one of claims 1-4, wherein said atrial pacing pulse is delivered about 100 milliseconds before said cardioversion shock therapy.

15. A method of reverting tachyarrhythmia in a patient's heart, comprising the steps of:
   detecting the presence of a tachyarrhythmia;
   delivering an atrial pacing pulse to the heart to depolarize the atrium and produce for a limited period of time an atrial refractory condition therein; and delivering cardioversion shock therapy to the heart during the period of said atrial refractory condition, whereby both the atrium and the ventricle of the heart will be simultaneously in a refractory condition immediately following the delivery of the cardioversion shock therapy.

16. A method of reverting tachyarrhythmia and providing bradycardia support pacing in a patient's heart, comprising the steps of:

detecting the presence of a tachyarrhythmia;

delivering a pacing pulse to the atrium of the heart to depolarize the atrium and produce for a limited period of time an atrial refractory condition therein;

delivering cardioversion shock therapy to the heart during the period of said atrial refractory condition, whereby both the atrium and the ventricle of the heart are simultaneously in a refractory condition immediately following the delivery of the cardioversion shock therapy;

determining that the tachyarrhythmia has been reverted; and, thereafter, delivering bradycardia support pacing to the heart when required.

17. A method according to claim 16 which includes, after the step of determining that the tachyarrhythmia has been reverted and before the step of delivering bradycardia support pacing, the further step of delaying the delivery of bradycardia support pacing for a period of time that is substantially longer than a normal bradycardia support pacing standby interval.

18. A method according to claim 17, wherein said period of delaying the delivery of bradycardia support pacing is between substantially two and substantially five seconds.

19. A method according to any one of claims 15-18, wherein said atrial pacing pulse is delivered in synchronism with the R-wave of the heart.

20. A method according to any one of claims 15-18, including the step of delivering antitachycardia pacing to the atrium.

21. A method according to any one of claims 15-18, including the step of delivering antitachycardia pacing to the ventricle.

22. A method according to any one of claims 15-18, including the step of delivering antitachycardia pacing to both the atrium and the ventricle.

23. A method according to any one of claims 15-18, wherein said cardioversion therapy includes a monophasic waveform.

24. A method according to any one of claims 15-18, wherein said cardioversion therapy includes a biphasic waveform.

25. A method according to any one of claims 15-18, wherein said pacing pulse to the atrium is delivered about 100 milliseconds before said cardioversion shock therapy.

26. A method according to claim 18, wherein said period of delaying the delivery of bradycardia support pacing is a fixed period.

27. A method according to claim 18, wherein said period of delaying the delivery of bradycardia support pacing is a programmable parameter.

* * * * *

UNITED STATES PATENT AND TRADEMARK OFFICE
CERTIFICATE OF CORRECTION

PATENT NO. : 5,074,301

DATED : December 24, 1991

INVENTOR(S) : Norma L. Gill

It is certified that error appears in the above-identified patent and that said Letters Patent is hereby corrected as shown below:

On the cover page, item [75] Inventor: change the spelling to the inventor"s name from "Norma L. Gill" to --Norma L. Gilli--.

Signed and Sealed this

Twenty-third Day of March, 1993

Attest:

STEPHEN G. KUNIN

*Attesting Officer*     Acting Commissioner of Patents and Trademarks